US008530157B2

(12) United States Patent
Peter et al.

(10) Patent No.: US 8,530,157 B2
(45) Date of Patent: Sep. 10, 2013

(54) SNP-DEPENDENT END LABELING METHOD

(75) Inventors: Brian Jon Peter, San Carlos, CA (US); Nicholas M. Sampas, San Carlos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 195 days.

(21) Appl. No.: 12/829,155

(22) Filed: Jul. 1, 2010

(65) Prior Publication Data
US 2012/0004123 A1 Jan. 5, 2012

(51) Int. Cl.
*C12Q 1/68* (2006.01)
*C12P 19/34* (2006.01)
*C12M 1/34* (2006.01)
*C12M 3/00* (2006.01)
*C07H 21/02* (2006.01)
*C07H 21/04* (2006.01)

(52) U.S. Cl.
USPC ....... 435/6.1; 435/6.11; 435/91.1; 435/287.2; 536/23.1; 536/24.3; 536/24.33

(58) Field of Classification Search
USPC .............. 435/6.1, 6.11, 6.12, 91.1, 91.2, 183, 435/283.1, 287.1, 287.2; 436/94, 501; 536/23.1, 24.3, 24.33, 25.3
See application file for complete search history.

(56) References Cited

U.S. PATENT DOCUMENTS

| 5,925,525 | A | 7/1999 | Fodor et al. |
| 6,306,643 | B1 | 10/2001 | Gentalen et al. |
| 6,309,823 | B1 | 10/2001 | Cronin et al. |
| 6,368,799 | B1 | 4/2002 | Chee |
| 6,468,744 | B1 | 10/2002 | Cronin et al. |
| 6,713,258 | B2 | 3/2004 | Kilian |
| 6,852,490 | B2 | 2/2005 | Gentalen et al. |
| 6,892,007 | B2 | 5/2005 | Chen |
| 7,011,949 | B2 | 3/2006 | Amorese et al. |
| 7,097,976 | B2 | 8/2006 | Kennedy |
| 7,211,384 | B2 | 5/2007 | Barrett et al. |
| 7,319,181 | B2 | 1/2008 | Vanavichit et al. |
| 2007/0128650 | A1 | 6/2007 | Schell et al. |
| 2009/0035762 | A1 | 2/2009 | Sampas |

FOREIGN PATENT DOCUMENTS

WO 9511995 A1 5/1995

OTHER PUBLICATIONS

Restrsiction endonuclease AlwN I from sciencegateway.org. Printed on Jun. 15, 2012.*
Kilian, et al. The fast and the cheap: SNP and DArT-based whole genome profiling for crop improvement. In the Wake of the Double Helix: From the Green Revolution to the Gene Revolution. Edited by: Tuberosa R, Phillips RL, Gale M. Bologna, Italy: Avenue media; 2005:443-461.
Wenzl, et al. Diversity arrays technology (DArT) for whole-genome profiling of barley. PNAS. 2004, vol. 101, No. 26, pp. 9915-9920.
U.S. Appl. No. 12/758,713, filed Apr. 12, 2010 (Specification, Claims, Abstract and Figures as filed); Peter et al. (2010) "Analysis of Single Nucleotide Polymorphisms Using End Labeling" (31 pgs).

* cited by examiner

Primary Examiner — Frank Lu

(57) ABSTRACT

Certain embodiments described in this disclosure relate to a method of sample analysis. In certain cases, the method comprises: a) contacting a genomic sample comprising double-stranded genomic DNA with a first restriction endonuclease that recognizes a nucleotide sequence that comprises a SNP site in the double stranded genomic DNA, wherein: i. the restriction endonuclease cleaves the genomic DNA at the sequence regardless of the allele of the SNP present at the SNP site; and ii. cleavage of the sequence by the restriction enzyme creates a 5' overhang that comprises the SNP site; b) contacting the digested genomic sample with a extension enzyme and a first labeled nucleotide that is used by the extension enzyme to fill in the overhang only if the overhang comprises a first allele of the SNP.

16 Claims, 2 Drawing Sheets

SEQUENCE LISTING

```
<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: (6)..(10)
<223> OTHER INFORMATION: n is a, c, g, or t

<400> SEQUENCE: 1 ggatcnnnnn                                                          10
```

```
<210> SEQ ID NO 2
<211> LENGTH: 10
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(10)
<223> OTHER INFORMATION: n is a, c, g, or t

<400> SEQUENCE: 2 cctagnnnnn                                                            10

<210> SEQ ID NO 3
<211> LENGTH: 10
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(10)
<223> OTHER INFORMATION: n is a, c, g, or t

<400> SEQUENCE: 3 gagtcnnnnn                                                            10

<210> SEQ ID NO 4
<211> LENGTH: 10
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(10)
<223> OTHER INFORMATION: n is a, c, g, or t

<400> SEQUENCE: 4 ctcagnnnnn                                                            10

<210> SEQ ID NO 5
<211> LENGTH: 11
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (6)..(11)
<223> OTHER INFORMATION: n is a, c, g, or t

<400> SEQUENCE: 5
cccgcnnnnn n                                                          11

<210> SEQ ID NO 6
<211> LENGTH: 11
<212> TYPE: DNA
<213> ORGANISM: Artificial Sequence
<220> FEATURE:
<223> OTHER INFORMATION: synthetic nucleotide sequence
<220> FEATURE:
```

-continued

```
<221> NAME/KEY: misc_feature
<222> LOCATION: (6)..(11)
<223> OTHER INFORMATION: n is a, c, g, or t

<400> SEQUENCE: 6
gggcgnnnnn n                                                                11
```

SNP-DEPENDENT END LABELING METHOD

INTRODUCTION

The human genome has several types of variation which confer genetic differences between individuals. Single nucleotide polymorphisms (SNPs) are sites of single base changes which vary in at least 1% of the population. Copy number variants (CNVs) are larger regions of DNA which are duplicated or deleted with respect to a reference genome.

Methods for the determination of SNP alleles and copy number measurements are important to the research community for improved understanding of disease mechanisms and progression, and to clinicians for diagnosis, especially in cytogenetics and cancer. Researchers could benefit from the development of a high throughput means for analyzing SNPs in human genomic DNA.

SUMMARY

Certain aspects of this disclosure relate to a method of sample analysis. In certain cases, the method comprises: a) contacting a genomic sample comprising double-stranded genomic DNA with a first restriction endonuclease that recognizes a nucleotide sequence that comprises a single nucleotide polymorphism (SNP) site in the double stranded genomic DNA, to provide a digested genomic sample, wherein: i. the restriction endonuclease cleaves the genomic DNA at the sequence regardless of the allele of the SNP present at the SNP site; and ii. cleavage of the sequence by the restriction enzyme creates a 5' overhang that comprises the SNP site; b) contacting the digested genomic sample with a extension enzyme and a first labeled nucleotide that is incorporated by the extension enzyme to fill in the overhang only if the overhang comprises a first allele of the SNP, to produce a labeled sample; c) hybridizing the labeled sample with a surface-tethered probe sequence that hybridizes to a nucleic acid fragment that comprises the SNP site; and d) determining whether the first allele of the SNP is present in the genomic sample, wherein the presence of the first allele in the sample is indicated by hybridization of a fragment comprising the labeled nucleotide to the surface-tethered probe sequence.

DEFINITIONS

Figure 1:
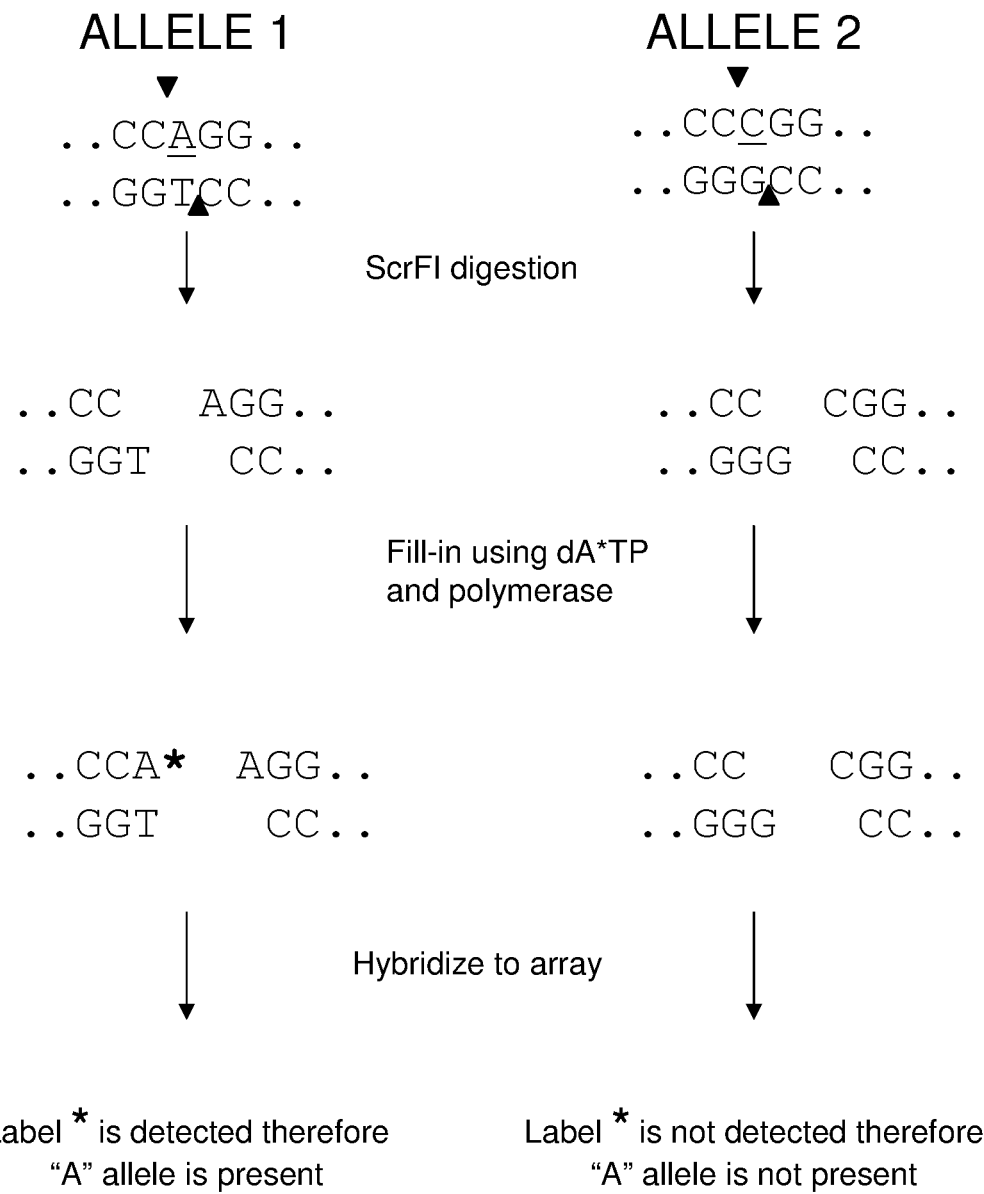
FIG. 1 schematically illustrates one embodiment in which an allele of a SNP is determined.

The term "sample", as used herein, relates to a material or mixture of materials, typically, although not necessarily, in liquid form, containing one or more analytes of interest.

The term "genome", as used herein, relates to a material or mixture of materials, containing genetic material from an organism. The term "genomic DNA" as used herein refers to deoxyribonucleic acids that are obtained from an organism. The term "genomic DNA" as used herein also encompasses deoxyribonucleic acids that derived from nucleic acids obtained from an organism, for example, cDNA derived from RNA obtained from an organism. The terms "genome" and "genomic DNA" encompass genetic material that may have undergone amplification, purification, or fragmentation. In some cases, genomic DNA encompasses nucleic acids isolated from a single cell, or a small number of cells. The "genome" in the sample that is of interest in a study may encompass the entirety of the genetic material from an organism, or it may encompass only a selected fraction thereof: for example, a genome may encompass one chromosome from an organism with a plurality of chromosomes.

The term "genomic region" or "genomic segment", as used herein, denotes a contiguous length of nucleotides in a genome of an organism.

The term "reference," as used herein refers to a genome, a genomic region, or a nucleotide acid to which a sample may be compared. In certain cases, the reference contains a region of known nucleotide sequence, e.g. a chromosomal region whose sequence is deposited at NCBI's Genbank database or other databases, for example. The reference may be the same species (e.g., where the species is human, or mouse, for example) as that of the sample analyzed in the subject method. The reference sample may represent the genome of an individual, or may represent either a physical pooling of the genomes of multiple individual or computational combination of the signals or ratios of signals from a number of individuals. A "reference" includes one or more samples that have been run earlier than a test sample, where data from the reference sample is processed to provide an estimate of what to expect if a test sample is heterozygous or homozygous for an allele of a SNP.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be surface-tethered, i.e., immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional or substantially two-dimensional (as well as a three-dimensional) arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 μm$^2$, or even smaller. For example, features may have widths (that is, diameter, for a round spot) in the range from a 5 μm to 1.0 cm. In other embodiments each feature may have a width in the range of 1.0 μm to 1.0 mm, usually 5.0 μm to 500 and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other more advanced models that depend on various parameters may also be used to predict $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are optimized to anneal an oligonucleotide of a sufficient length to a probe, e.g. an oligonucleotide that is not nicked and has a contiguous length of at least 20 nucleotides (e.g. at least 30, at least 40, up to at least 50 or more) complementary to a nucleotide sequence of the probe. The hybridization conditions provide for dissociation of duplexes that anneal over a short length of region (e.g. less than 50, less than 40, less than 30, or less than 20 contiguous nucleotides) but not dissociation of duplexes formed between an un-nicked strand and its respective probe. Such conditions may differ from one experiment to the next depending on the length and the nucleotide content of the complementary region. In certain cases, the temperature for low-stringency hybridization is 5°-10° C. lower than the calculated $T_m$ of the resulting duplex under the conditions used. Details on the hybridization conditions suitable for use in certain embodiments in the present disclosure may be found in US Patent Publication 20090035762, the disclosure of which is incorporated herein by reference.

The term "homozygous" denotes a genetic condition in which identical alleles reside at the same loci on homologous chromosomes. In contrast, "heterozygous" denotes a genetic condition in which different alleles reside at the same loci on homologous chromosomes.

"Color", as used herein, refers to the wavelength at which the emission spectrum of a label reaches a maximum. For example, a label that is referred herein as red has an emission spectrum with a maximum at about 650 nm.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

As used herein, the term "single nucleotide polymorphism", or "SNP" for short, refers to a phenomenon in which two or more alternative alleles (i.e., different nucleotides) are present at a single nucleotide position in a genomic sequence at appreciable frequency (e.g., often 1%) in a population. In some cases, SNPs may be present at a frequency less than 1% in a population. As used herein, the term SNP may include these "rare SNPs" (present at a frequency less than 1% in a population) or even "single nucleotide variants" (SNVs) that have only been detected in one or a few samples to date.

As used herein, the term "SNP site" denotes the position of a SNP in a genomic sequence. A SNP site may be indicated by genomic coordinates. The nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's online dbSNP database, and the online database of the International HapMap Project; see also Teufel et al 2006 *Current bioinformatics tools in genomic biomedical research* Int. J. Mol. Med. 17:967-73).

As used herein, the term "SNP sequence" refers to is a naturally-occurring nucleotide sequence that contains a SNP site. Since at least two alleles my exist at a given SNP site, at least a pair of SNP sequences correspond to each SNP site, both of which contain the same flanking sequences, but the nucleotide at the SNP site differs. A SNP sequence can be of any length, and in particular embodiments may be up to 5, 10, 15, 20, 25, 30, 35 or 40 nucleotides or more, e.g., up to 50-80 nucleotides or more. In particular embodiments, the sequences that flank a SNP site on either side may be at least 2, 3, 4, 5, 6, 7, 8, 9, 10, 11, 12, 13, 14, 15, 16, 17, 18, 19, 20 nucleotides long, or more, e.g., 15-30 or 15-40 nt, or any range in between (such as 3-15, 5-12, 9-16, etc.).

As used herein, the term "SNP allele" refers to the identity of the nucleotide at a SNP site (e.g., whether the SNP site has a G, A, T or C or a deletion or insertion or a small number of nucleotides). A "first allele" and a "second allele" of a SNP are different alleles, i.e., they have different nucleotides at the SNP site.

As used herein, the term "restriction enzyme" refers to a site-specific restriction endonuclease that cuts double stranded DNA at a specific nucleotide sequence. Restriction enzymes recognize a specific nucleotide sequences in double-stranded DNA. A restriction enzyme may cleave double stranded DNA to produce blunt ends or sticky ends that may have a 3' or 5' overhang of 1, 2, 3, or 4 nucleotides, for example. In some cases, a restriction enzyme may cleave a sequence that lies outside the recognition sequence for that enzyme, for example, a specific number of nucleotides away from the recognition site. TypeIIS, TypeIIG, and TypeIII restriction enzymes represent examples of classes of restriction enzymes that cleave outside of their recognition sequence, and which may be used in embodiments. Further information on TypeIIS, TypeIIG, and TypeIII restriction enzymes may be found in the REBASE online restriction enzyme database.

The term "recognition site" is the sequence of nucleotides recognized by a restriction enzyme. The recognition site for a restriction enzyme may be in the range of 4-8 or more base pairs in length. In certain cases, a recognition site may be 4, 5 or 6 base pairs in length, or more. Restriction enzymes that cut within their recognition site as well restriction enzymes that cut outside of their recognition site (e.g., Type IIA, Type IIB, Type IIS, and Type IIG restriction enzymes) may be employed herein.

As used herein, a "cleavage site" of a restriction enzyme is defined by the phosphodiester bonds broken during cleavage of a double stranded DNA using a restriction enzyme. If a restriction enzyme cleaves to produce an overhang, then the cleavage site is defined by the nucleotides in the overhang, i.e., the single stranded portion of the overhang. For example, for a restriction enzyme that cleaves to produce a 5' overhang, the cleavage site of the enzyme is defined by the nucleotides that extend out past the recessed 3' end of the DNA.

For some enzymes, the cleavage site is within the recognition site for the enzyme. For other enzymes, the cleavage site is not in the recognition site.

As used herein, the term "variable nucleotide" in the context of a recognition site or cleavage site of a restriction enzyme, refers to a position that can position that can be G, A, T or C. For example, if cleavage of a sequence by a restriction endonuclease results in a cleavage site that contains a variable nucleotide, the restriction enzyme cleaves to produce an overhang in which at least one of positions is a G, A, T or C. For example, and as will be described in greater detail later in this disclosure, the recognition sites and cleavage sites for Hpy178III, ScrFI and Fnu4HI (as well as many other enzymes) contain a variable nucleotide since these enzymes cleave at a sequence that contains an "N", where N can be G, A, T or C. In some cases, a variable nucleotide denoted by a different letter may only vary between 2 or sometimes 3 nucleotides. For example, sequences containing a Y may have either C or T at that position, sequences containing a R may contain either an A or a G at that position, sequences containing an S may contain either a G or a C at that position, sequences containing a W may contain either an A or T at that position, sequences containing a B may contain a G, C, or T at that position, and sequences containing an H may contain an A, C, or T at that position.

As used herein, a restriction enzyme that "recognizes a nucleotide sequence that comprises a single nucleotide polymorphism (SNP) site" or a grammatical equivalent thereof, refers to an enzyme that contains a SNP site in its recognition site. The SNP site may be in the recognition site or the cleavage site of the restriction enzyme.

As used herein, the phrase "cleaves said genomic DNA at a sequence regardless of the allele of the SNP present at said SNP site" refers to cleavage that is independent of the identity of the nucleotide at the SNP site, i.e., cleavage that takes place if the nucleotide at the SNP site is G, A, T or C.

As used herein, a "5' overhang that comprises a SNP site" or a grammatical equivalent thereof refers to the product of a restriction enzyme digestion that has a recessed 3' end and an overhanging 5' end, where the SNP nucleotide (i.e. the nucleotide that varies, depending on the allele of the SNP) is present in the nucleotides of the overhanging 5' end. In particular cases, the SNP nucleotide may be immediately adjacent to the nucleotide that base pairs with the 3' end nucleotide of an overhanging 5' end.

As used herein, the term "filling in a 5' overhang" or a grammatical equivalent thereof refers to the extension of the recessed 3' end of a 5' overhang with at least one nucleotide by a extension enzyme.

If a labeled nucleotide is "used by said extension enzyme to fill in a overhang only if the overhang comprises a first allele of said SNP" or a grammatical equivalent thereof, then the nucleotide used may either be complementary with the SNP site of an overhang (in which case it will be used by the extension enzyme and incorporated into the DNA, thereby labeling the DNA), or not complementary with the SNP site (in which case it will not be used by the extension enzyme).

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Genome Analysis

Some of the general principles of the subject method may be described with reference to FIG. 1, which schematically illustrates one embodiment of the method. As shown in FIG. 1, whether or not a genomic sample contains a first allele of a SNP ("allele 1", in which the SNP nucleotide is an underlined "A") can be determined by digesting the genomic sample with a restriction endonuclease that cleaves to produce a 5' overhang containing the SNP site. As illustrated in FIG. 1, the selected restriction endonuclease: a) cleaves the genomic DNA at the sequence regardless of the allele of the SNP present at the SNP site (i.e., regardless of whether the sample contains the first allele of the SNP (i.e., "allele 1") or the second allele of the SNP ("allele 2", in which the SNP nucleotide is an "C", which is underlined); and b) cleaves to produce a 5' overhang that contains the SNP site. Cleavage by the enzyme at the cleavage site is not dependent on the allele of the SNP. In the embodiment illustrated in FIG. 1, the enzyme ScrF1 is used although, as will be discussed below, many other restriction enzymes are suitable for use in the method.

In the embodiment shown in FIG. 1, cleavage of both alleles of the SNP produces an overhang containing the SNP site. The next step of the method includes contacting the digested genomic sample with an extension enzyme and a first labeled nucleotide that is used by the extension enzyme to fill in the overhang only if the overhang contains one allele of the SNP rather and not another, to produce a labeled sample. In the embodiment shown in FIG. 1, dA*TP (in which the "*" is a detectable label) is used, which is only incorporated by the extension enzyme if the SNP allele is an "A". Thus, incorporation of the label is dependent upon the identity of the SNP allele present in the cleavage site. The presence or absence of an incorporated label can be detected by hybridizing the labeled sample with a surface-tethered probe sequence, e.g., a probe on an array, that hybridizes to a nucleic acid fragment produced by the digestion and that contains the SNP site. In the embodiment shown in FIG. 1, detection of the label * indicates that the "A" allele of the SNP is present in the sample. If label * is not detected than the "A" allele of the SNP is not present in the sample.

Labeled and unlabeled nucleotides may be incorporated by different extension enzymes. The extension enzymes should be template-dependent in that they incorporate the nucleotide that is complementary to the nucleotide in the template strand at that position. Examples of extension enzymes include DNA polymerases and DNA ligases. For example, Klenow fragment polymerase may be used. For example, T4 DNA ligase may be used. Many other suitable examples of extension enzymes may be used.

Figure 2:
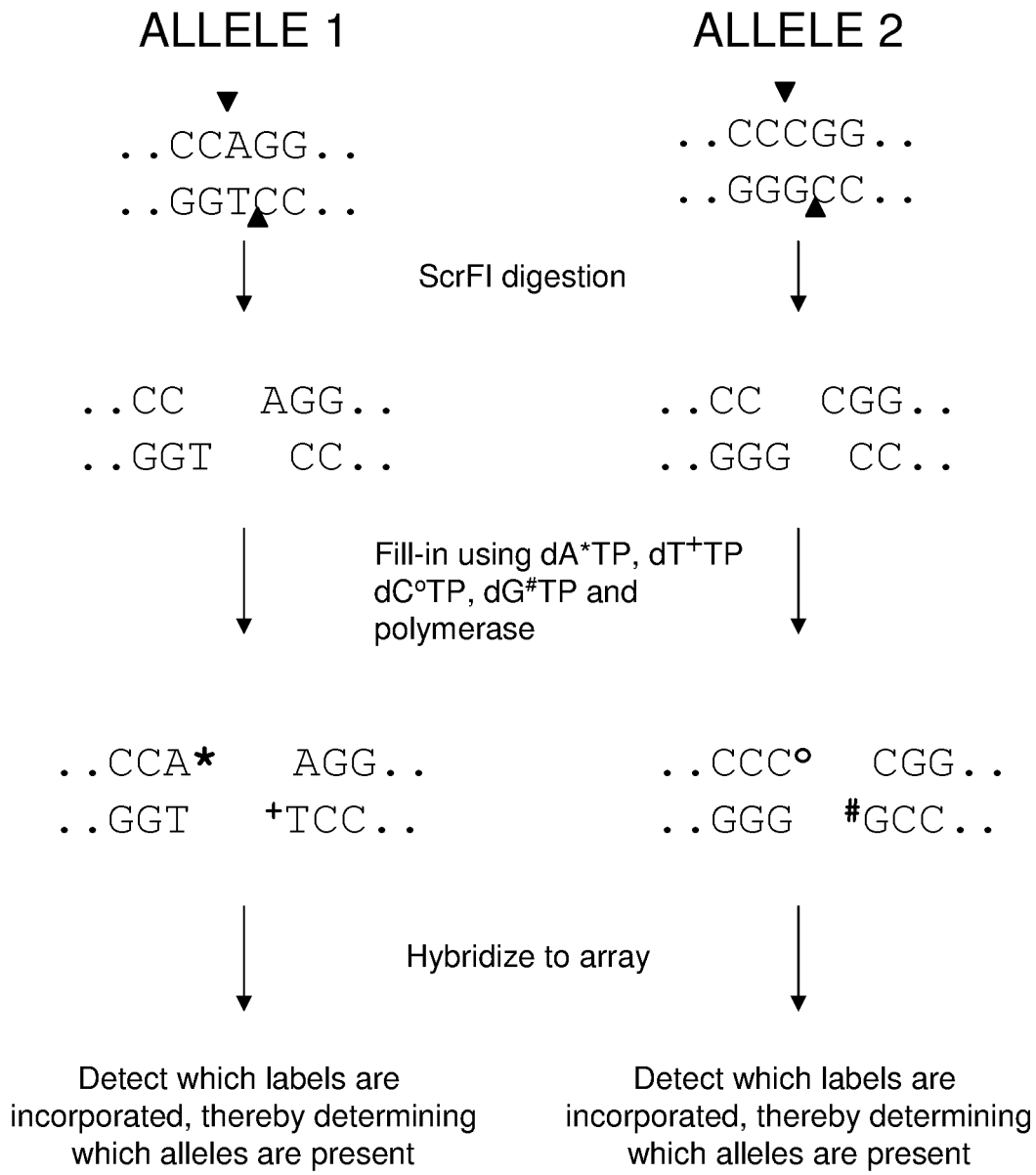
FIG. 2 schematically illustrates a second embodiment in which an allele of a SNP is determined.

As would be apparent from the above, a sample may be further labeled with at least a second, third and/or fourth label, which labels are distinguishable from the first label and distinguishable from one another, and where each of the labels is linked to a different nucleotides (i.e., G, T and/or C, if the initial nucleotide is an A). In one embodiment, a pair of distinguishable labeled nucleotides may be employed in the method (e.g., a G/C pair, an A/T pair, a G/T pair, a C/T pair, a G/A pair or a C/A pair, etc), and the identity of the allele of the SNP may be determined by detecting both of the labels. FIG. 2 illustrates an embodiment in which the digested genomic sample is labeled with all four nucleotides, each of which is distinguishably labeled (the labels being "*", "+", "o" and "#"). In this method, all of the overhangs are filled in, and the allele present in all of the cut SNP sites can be determined by identifying which labels are associated with the probe. In this method, each allele of triallelic SNPs (e.g., a SNP which may be an A, G, or T) can be determined.

In a diploid genome, multiple alleles may be present simultaneously for heterozygous SNPs in an individual sample, thus in such cases different labels would be simultaneously detected. Normalized signal ratios for two distinct labels within some range, e.g. 0.25-0.75 may indicate the presence of heterozygous SNP, whereas above and below such a range may indicate the presence of that SNP in a homozygous state. By logical extension, in regions of the genome that are either segmentally duplicated or copy-number variant other theoretical ratio values e.g. 1/3, 2/3, 1/4, 3/4, 1/5, etc. may also be measured. This method enables the direct measurement of allele-specific copy number.

Suitable detectable labels are known in the art and need not be described in detail herein. Briefly, exemplary detectable components include fluorophores, fluorescence quenchers, affinity tags, e.g. biotin, crosslinking agents, chromophores, colloidal gold particles, beads, quantum dots, etc. In certain embodiments, the detectable label, such as biotin, may require incubation with a recognition element, such as streptavidin, or with secondary antibodies to yield detectable signals. In other embodiments, the detectable label, such as a fluorophore, may be detected directly without performing additional steps.

Fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g. umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used include: pyrene, coumarin, diethylaminocoumarin, FAM, fluorescein chlorotriazinyl, fluorescein, R110, eosin, JOE, R6G, tetramethylrhodamine, TAMRA, lissamine, ROX, napthofluorescein, Texas red, napthofluorescein. Distinghishable dyes include Cy3 and Cy5, etc. (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (*Ann Clin Biochem.* 39:114-29, 2002).

The choice of nucleotides employed in the labeling mix used in the method may vary dependent upon which enzyme is used and the SNP alleles of interest. In some embodiments, the labeling mix may contain one more labeled chain terminator nucleotides (e.g., labeled dideoxynucleotides), one or more labeled non-chain terminator nucleotides, or a mixture of the two, as desired. Labeled chain terminators can be used to incorporate a single site-specific label and block further extension. In one example, the labeling mix may contain a first and a second labeled chain terminator nucleotides, the first and second labeled chain terminator nucleotides may be dideoxyadenine and dideoxyguanine, respectively. The adenine chain terminator may be labeled with a first label, while the guanine chain terminator may be labeled with a second label. In another example, four-color labeling may employ first, second, third and fourth labeled chain terminators derived from A, G, C, and T, respectively, in which each of the first, second, third, and fourth labels emits a distinguishable signal. The reagent mix may also contain labeled as well as unlabeled nucleotides.

In certain embodiments, the labeled sample may be further fragmented prior to hybridization using, e.g., a restriction enzyme, chemical cleavage or physical cleavage, (by shearing, nebulization, sonication, etc.) prior to being hybridized with the surface tethered probe sequence.

In addition to being end-labeled using the above method, the labeled sample may be labeled by other means, e.g., by labeling the backbone of the nucleic acid, e.g., by nick translation, random priming or ULS labeling. In certain embodiments, the nucleic acid may be labeled by Universal Linkage System (ULS™, KREATECH Diagnostics) van Gijlswijk et al (Universal Linkage System: versatile nucleic acid labeling technique Expert Rev. Mol. Diagn. 2001 1:81-91). In brief, ULS™ labeling is based on the stable binding properties of platinum (II) to nucleic acids. The ULS molecule consists of a monofunctional platinum complex coupled to a detectable molecule of choice. Standard methods may be used for labeling the oligonucleotide, for example, as set out in Ausubel, et al, (*Short Protocols in Molecular Biology,* 3rd ed., Wiley & Sons, 1995) and Sambrook, et al, (*Molecular Cloning: A Laboratory Manual, Third Edition,* (2001) Cold Spring Harbor, N.Y.). In embodiments in which a ULS labeling protocol is employed, the labeled DNA may be further fragmented as part of the ULS labeling method, which will ensure that there is only one end-label per fragment.

Suitable restriction enzymes cleave to produce a 5' overhang having a variable nucleotide (i.e., an "N"). In certain cases, the recognition site for the enzyme may also contain the variable nucleotide. Exemplary enzymes that can be used in the method are set forth below in Table 1, although other enzymes with the same general characteristics may also be used.

TABLE 1

Partial list of restriction enzymes that cleave to produce a 5' overhang that contains a SNP site.

```
Hpy178III
T C/N N G A
A G N N/C T
ScrFI
C C/N G G
G G N/C C
Fnu4HI
G C/N G C
C G N/C G
BmgT120I
G G/N C C
C C N/G G
BspPI
G G A T C N N N N/N    (SEQ ID NO: 1)
C C T A G N N N N N/   (SEQ ID NO: 2)
PpsI
G A G T C N N N N/N    (SEQ ID NO: 3)
C T C A G N N N N N/   (SEQ ID NO: 4)
FauI
C C C G C N N N N/N N  (SEQ ID NO: 5)
G G G C G N N N N N N/ (SEQ ID NO: 6)
Hpy188III
T C/N N G A
A G N N/C T
DdeI
C/T N A G
G A N T/C
HinfI
G/A N T C
C T N A/G
Sau96I
G/G N C C
C C N G/G
```

Probe sequences that may be employed in this method can hybridize to a sequence contained in a fragment produced by the restriction enzyme used. In particular embodiments, the probe may in the range of 30 to 100 nucleotides in length, and in certain cases may hybridize to a sequence that is within 500 nucleotides (e.g., 10 to 200 nucleotides of the end label). Exemplary methods for designing such probes, and hybridization conditions for performing the instant hybridization step may be found in U.S. patent application publication US20040191813, which is incorporated by reference for all purposes.

In certain cases, the subject method may include comparing data to a reference. In some cases, the reference sample may be contacted to an array to provide hybridization signals as a control. The reference sequence may be a sequence derived from an identified source or from the same species as the genomic sample under study. The source of the reference may be known to be homozygous or heterozygous for a particular genomic locus of interest. In certain cases, the source may be wild-type for a genomic locus of interest. The source may contain an allelic variant of interest. In certain cases, the reference sequence may be known so that the alleles of the single nucleotide polymorphisms are known. In particular embodiments, the reference sample may be a mixture of a population of different individuals in which the SNP status is averaged out.

Arrays for carrying out the subject method may contain a plurality of probes each hybridizing to a sequences that flank a digestable SNP site in a mammalian genome. In certain embodiments, there may be at least 5,000, at least 10,000, at least 100,00 or at least 100,000 or more of such probes on an array. The array may also contain SNP spanning probes as described in U.S. Patent Application Pub. No. 20090035762. Use of such an array allows the simultaneous analysis of an equivalent number of probes.

In certain embodiments, the probes are designed such that duplexes formed by hybridization to the probes are $T_m$-matched. In some embodiments, the array contains duplicates of probes. In some embodiments, the array may contain multiple sets (e.g., at least 10, at least 100, at least 1,000, at least 10,000 or at least 50,000 or more sets) of probes, where each set of probes is designed for analysis of a single SNP site and may contain as few as two and as many as 4 or 8 probes.

Reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Santa Clara, Calif. Other suitable apparatus and methods are described in U.S. Pat. No. 7,205,553 "Reading Multi-Featured Arrays" by Dorsel et al.; and U.S. Pat. No. 7,531,303 "Interrogating Multi-Featured Arrays" by Dorsel et al., both disclosures of which are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition). The results of the reading (processed or not) may be forwarded (such as by communication) to a remote location if desired, and received there for further use (such as further processing).

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

In some embodiments, the method may further comprise determining whether the DNA sample is homozygous or heterozygous for the first allele of the SNP, and in further embodiments, the method may further comprise determining the copy number of the fragment containing the SNP. In certain embodiments, the allelic state of a plurality of SNPs in a genomic region may be determined, and loss-of-heterozygosity (LOH) analysis may be performed. In this way, conditions such as uniparental disomy (UPD) may be detected.

The method described above may be combined with the method described in U.S. Patent Application Pub. No. 20090035762 to provide an orthogonal analysis of a SNP site, without impacting the accuracy of the method described in U.S. Patent Application Pub. No. 20090035762. U.S. Patent Application Pub. No. 20090035762 is incorporated herein for disclosure of such a method, including exemplary probe design protocols, sample preparation protocols, sample labeling protocols, and data analysis protocols. This method generally involves a method that comprises: a) contacting a first DNA sample comprising genomic DNA with a first restriction enzyme to provide a digested sample, wherein: i) the DNA sample may comprise a sequence comprising a SNP site; and ii) the first restriction enzyme cleaves the sequence only if a first allele of a SNP is present at the SNP site; b) hybridizing the digested sample to a microarray comprising a probe sequence that is complementary to the sequence comprising the cleavage site; c) comparing the amount of hybridization between the digested sample and the probe sequence to the amount of hybridization between a reference sample and the probe sequence, and d) determining whether the first allele of the SNP is present in the DNA sample, wherein the relative hybridization of the digested sample to the probe as compared to the reference sample indicates whether the first allele of the SNP is present in the DNA sample. Cleavage of the sequence at the cleavage site by the first restriction enzyme results in less hybridization of the digested sample relative to a sample in which the sequence is undigested. In this method, the probes spanning the cleavage site are used to measure the amount of uncleaved DNA at a cleavage site. If the cleavage site is cut by the restriction enzyme site, a loss of signal is detected. Therefore, hybridization to the uncut DNA to a probe is measured, and the amount of cut DNA is deduced from the loss of signal. By combining this method with an additional end-labeling-based method (using different labels that are distinguishable) and additional array probes, as described above, further alleles may be identified and/or confirmed).

In particular embodiments and as noted above, the instant method may be performed in parallel with the method described in published patent application US20090035762, adding a different, independent, detection method for the same SNP sequence in that the allele of a SNP can be more accurately determined.

In certain embodiments and as noted above, the subject method further includes measuring the copy number of specific nucleotide sequences in combination with determining the SNP based on the embodiments described above. In certain cases, the analysis of copy number may also be carried out using the same array, where the hybridization signals of a sample are also used to calculate copy number of sequences in the genomic sample. Additional features may be optionally included on the array to facilitate the analysis. Methods and composition used for assessing copy numbers are described in detail in U.S. Patent Application Pub. Nos. 20070238106 and 20070238108, disclosures of which are incorporated herein by reference.

Kits

Also provided by the present disclosure are kits for practicing the method as described above. The subject kit contains reagents for performing the method described above and in certain embodiments may contain a restriction enzyme (i.e., a restriction enzyme that cleaves genomic DNA at a sequence comprising a SNP site, e.g., of the human genome, regardless of the allele of the SNP present at said SNP site, wherein cleavage of the sequence by said restriction enzyme creates a 5' overhang that comprises the SNP site), and reagents for filling in said 5' overhang that include a polymerase and a labeled nucleotide, wherein the labeled nucleotide is used by said extension enzyme to fill in said overhang only if the overhang comprises a first allele of said SNP. The kit may optionally include a surface tethered probe sequence (e.g., an array) that hybridizes to a fragment comprising said SNP site. The kit may also contain a reference nucleic acid to which results obtained from a test sample may be compared.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to above-mentioned components, the subject kit may include software to perform comparison of a collected hybridization signal with another.

Utility

The subject method finds use in a variety of applications, where such applications generally include nucleic acid detection applications in which the presence of a particular nucleotide sequence in a given sample is detected at least qualitatively, if not quantitatively. In general, the above-described method may be used in order to determine the allele of a SNP in a genomic DNA.

Since labeling is sequence dependent, the presence or absence of a label in specific locations on double-stranded DNA provides the identity of the allele at a SNP site. By identifying the incorporated label, the identity of the SNP allele may be determined. Since most animal cells are diploid (and therefore contain two copies of each genomic site), the method may be used to determine if the genome is homozygous for either a first or a second SNP allele (in which a single incorporated label will be identified at a SNP site), or heterozygous for the first and second SNP alleles (in which two incorporated labels will be incorporated at a SNP site). As such, in some cases, the genotype of the SNP locus may also be determined based on the ratio of hybridization signals from a single sample.

Other assays of interest which may be practiced using the subject method include: genotyping, scanning of known and unknown mutations, gene discovery assays, genomic structural mapping, loss-of-heterozygosity analysis, paternity testing, differential gene expression analysis assays, nucleic acid sequencing assays, sample identity, disease diagnosis and prognosis, and the like.

The data of SNP alleles identified through the use of the subject method can be collected and compared to a set of known SNPs associated with a disease or biological condition with the purpose of identifying an unknown source, genotyping, predicting a biological condition. This might represent comparison between SNPs coming from variants of a region to a reference. Identification of one or more SNPs in a sample genome may be useful for a wide variety of investigations, such as identifying origin of a crop, identifying species of fish or other animals, identifying pathogens, diagnosing human diseases, investigating cancer lineages or distinguishing between a finite number of known genotypes, etc.

In certain cases, the genomic sample under study may be derived from a sample tissue suspected of a disease or infection. Performing the subject method to analyze the genomic sample from such sample tissues would be useful for disease diagnosis and prognosis. Patents and patent applications describing methods of using arrays in various applications include: 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Since the nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome* BMC Bioinformatics 5:33; McCarthy et al 2000 *The use of single-nucleotide polymorphism maps in pharmacogenomics* Nat Biotechnology 18:505-8) and are available in public databases (e.g., NCBI's online dbSNP database, and the online database of the International HapMap Project; see also Teufel et al 2006 *Current bioinformatics tools in genomic biomedical research* Int. J. Mol. Med. 17:967-73), choosing an enzyme and designing probes should be well within the skill of one of skilled in the art.

The above described applications are merely representations of the numerous different applications for which the subject array and method of use are suited. In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of sample analysis, comprising:
   a) contacting a genomic sample comprising double-stranded genomic DNA with a first restriction endonuclease that recognizes a nucleotide sequence that comprises a single nucleotide polymorphism (SNP) site in said double stranded genomic DNA, to provide a digested genomic sample, wherein:
   i) said restriction endonuclease cleaves said genomic DNA at said sequence regardless of the allele of the SNP present at said SNP site; and
   ii) cleavage of said sequence by said restriction endonuclease creates a 5' overhang that comprises said SNP site;
   b) contacting said digested genomic sample with an extension enzyme and a first labeled nucleotide that is incorporated at said SNP site by said extension enzyme only if said overhang comprises a first allele of said SNP, thereby producing a labeled sample;
   c) hybridizing said labeled sample with a surface-tethered probe sequence that hybridizes to a nucleic acid fragment that comprises said SNP site; and
   d) determining whether the first allele of the SNP is present in the genomic sample, wherein the presence of hybridization of said labeled sample to said surface-tethered probe sequence indicates the presence of the first allele in the sample.

2. The method of claim 1, wherein the recognition site for said restriction enzyme comprises a variable nucleotide.

3. The method of claim 1, wherein said first restriction enzyme is ScrF1.

4. The method of claim 1, wherein said contacting step b) further comprises contacting said digested genomic sample with a second labeled nucleotide that that is incorporated into said overhang by said extension enzyme only if said overhang comprises a second allele of the SNP.

5. The method of claim 1, further comprising determining whether said genomic sample is homozygous or heterozygous for said first allele.

6. The method of claim 1, wherein said genomic sample comprises human genomic DNA.

7. The method of claim 1 further comprises fragmenting said labeled sample prior to said hybridizing step c).

8. The method of claim 1, wherein said surface-tethered probe sequence does not comprise the SNP site.

9. The method of claim 1 further comprises digesting said genomic sample with a second restriction endonuclease that has a different recognition sequence to said first restriction endonuclease and that cleaves said genomic DNA at SNP sites that are different to those cleaved by the first restriction endonuclease.

10. The method of claim 1, wherein said double-stranded genomic DNA is isolated directly from a cellular sample.

11. The method of claim 1, wherein said double-stranded genomic DNA comprises products amplified from a cellular sample.

12. The method of claim 1, wherein said determining step d) comprises comparing results obtained from said hybridizing step c) to results obtained from a genomic sample control.

13. The method of claim 12, wherein said control is a reference sample that has a known allele of said SNP at said SNP site.

14. The method of claim 1, wherein said sample comprises a selected fraction of the total genomic DNA of an organism.

15. The method of claim 1, wherein said labeled nucleotide is a fluorescently-labeled nucleotide.

16. The method of claim 1, wherein said labeled nucleotide is a labeled chain-terminator nucleotide.

* * * * *